United States Patent
Asgeirsson (10) Patent No.: US 7,438,843 B2
(45) Date of Patent: Oct. 21, 2008

(54) METHOD AND KIT FOR MAKING PROSTHETIC SOCKET

(75) Inventor: Sigurdur Asgeirsson, Gardabaer (IS)

(73) Assignee: Ossur hf, Reykjavik (IS)

( * ) Notice: Subject to any disclaimer, the term of this patent is extended or adjusted under 35 U.S.C. 154(b) by 0 days.

(21) Appl. No.: 11/819,536

(22) Filed: Jun. 28, 2007

(65) Prior Publication Data

US 2008/0004715 A1      Jan. 3, 2008

Related U.S. Application Data (60) Provisional application No. 60/817,346, filed on Jun. 30, 2006.

(51) Int. Cl.
*A61F 2/78* (2006.01)
*B29C 70/48* (2006.01)

(52) U.S. Cl. ............... 264/257; 264/DIG. 30; 425/2

(58) Field of Classification Search ............ 425/2; 264/257, DIG. 30
See application file for complete search history.

(56) References Cited

U.S. PATENT DOCUMENTS

| | | | |
|---|---|---|---|
| 3,823,208 A | 7/1974 | Asbelle et al. | |
| 4,783,293 A | 11/1988 | Wellershaus et al. | |
| 5,156,631 A | 10/1992 | Merlette | |
| 5,503,543 A | 4/1996 | Laghi | |
| 5,718,925 A | 2/1998 | Kristinsson et al. | |
| 5,885,509 A | 3/1999 | Kristinsson | |
| 5,888,231 A * | 3/1999 | Sandvig et al. | ............... 623/36 |
| 5,971,729 A | 10/1999 | Kristinsson et al. | |
| 5,972,036 A | 10/1999 | Kristinsson et al. | |
| 5,980,576 A * | 11/1999 | Graf et al. | ............... 623/33 |
| 6,156,071 A | 12/2000 | Biedermann et al. | |
| 6,416,703 B1 * | 7/2002 | Kristinsson et al. | ......... 264/257 |
| 6,991,444 B1 | 1/2006 | Laghi | |
| 2002/0087216 A1 | 7/2002 | Atkinson et al. | |
| 2004/0076848 A1 | 4/2004 | Shirer | |
| 2005/0173829 A1 * | 8/2005 | Taylor, Sr. | ............... 264/222 |

FOREIGN PATENT DOCUMENTS

SU           1419707           8/1988

OTHER PUBLICATIONS

Jerome J. M. Demoulin, "Welcome to . . . Resin Transfer Molding (RTM) Page" <<http://research.et.byu.edu/acme/rtm2.html>>, dated Apr. 13, 2006.
"Resin Transfer Molding", <<http://www.ams.sunysb.edu/~tangerma/RTM/rtm.html>>, dated Apr. 13, 2006.

* cited by examiner

*Primary Examiner*—Robert B Davis
(74) *Attorney, Agent, or Firm*—Bacon & Thomas, PLLC (57) ABSTRACT

A method and kit for forming a definitive prosthetic socket directly on a residuum without the use of a water hardenable material. A chamber surrounding a web of braided fibers is created on the residuum via the use of inner and outer protective sheaths. A hardenable or curable material for forming the prosthetic socket is injected into the chamber around the web. Pressure is applied around the chamber to form the definitive prosthetic socket.

20 Claims, 14 Drawing Sheets

METHOD AND KIT FOR MAKING PROSTHETIC SOCKET

This application claims the benefit of U.S. Provisional Application No. 60/817,346, filed Jun. 30, 2006.

FIELD OF THE INVENTION

The present invention relates generally to the field of prosthetic limbs, and more particularly to a definitive prosthesis socket for fitting residual limbs to prostheses and a kit and a method of forming the definitive prosthesis socket directly on the residual limb.

BACKGROUND

Definitive sockets for fitting prostheses to residual limbs of amputees are made by various processes in accordance with prior art techniques. For example, numerous techniques have been developed that involve first, creating a negative mold of the residual limb, second, creating a positive mold from the negative mold, third, modifying the positive mold to provide relief for sensitive areas of the residuum, and fourth, forming the prosthesis socket using the modified positive mold. This technique involves numerous steps, and the negative and positive molds are typically created using Plaster-of-Paris. Some examples of this technique are embodied in U.S. Pat. No. 5,503,543, granted Apr. 2, 1996; and U.S. Pat. No. 6,991,444 granted Jan. 31, 2006, both to Laghi.

Another technique used to form prosthetic sockets is to reduce the steps in the above process by forming the socket directly on the residual limb without creating both a negative and a positive mold. This technique can be implemented in a variety of ways.

For example, U.S. Pat. No. 5,718,925, granted Feb. 15, 1998; U.S. Pat. No. 5,971,729, granted Oct. 26, 1999; U.S. Pat. No. 5,972,036, granted Oct. 26, 1999; and U.S. Pat. No. 6,416,703 granted Jul. 9, 2002, all to Kristinsson et al., and all herein incorporated by reference, all disclose a method of forming a definitive prostheses socket directly upon a residual limb. In the method, a web-like tubular braided carbon fiber sleeve that is pre-impregnated with a water curable resin is soaked in water and placed upon the residuum. The sleeve is pressure cast in a known manner using the ICECAST™ system made by Össur hf of Reykjavik, Iceland, and described in U.S. Pat. No. 5,885,509, granted Mar. 23, 1999 to Kristinsson, and herein incorporated by reference.

U.S. Pat. No. 5,980,576, granted Nov. 9, 1999 to Graf et al., discloses another method of forming a prosthetic socket directly on a residuum. A prosthetic liner is placed on the residuum, and pads are appropriately placed around the liner. Plastic wrap is applied around the liner to hold the pads in place. A knit fabric is then rolled over the liner, pads and plastic wrap. Finally, a resin impregnated fabric sock is soaked in water and applied over the knit fabric. The technician manually manipulates the fabric sock, and then plastic wrap and a resilient bandage can be applied over the fabric sock.

U.S. Pat. No. 6,156,071, granted Dec. 5, 2000 to Biedermann et al., discloses yet another method of forming a prosthetic socket on a residuum. A double walled tubular fabric is impregnated with a resin, such as polyurethane. The fabric is then dipped into activating water and pulled over the residuum, which may be covered with a prosthetic liner. The fabric may then be pressed against the residuum.

All of the above techniques for forming a mold or a prosthetic socket require access to water to activate the hardenable material used to form the prosthetic socket.

Another method of forming a prosthetic socket directly on the residuum is disclosed in U.S. Pat. No. 4,783,293, granted Nov. 8, 1988 to Wellershaus et al. The method involves placing a plastic sheet on the residuum and thermoforming the sheet by applying elevated temperatures to the sheet.

In yet another method of forming a prosthetic socket directly on the residuum, disclosed in U.S. Pat. No. 3,823,208 granted Jul. 9, 1974 to Asbelle et al., ultraviolet light is used to polymerize a fiberglass bandage on the residuum.

While many solutions for forming prosthetic socket exist, none of the prior art references disclose a kit and process of forming a prosthetic socket directly on the residuum, where a chamber is created around a web of material that is not pre-impregnated with a water hardenable resin or material, and a hardenable material is injected into the chamber.

The disclosed kit and process for forming a prosthetic socket overcome a number of disadvantages present in the prior art, such as reducing the complexity and steps required to form a prosthetic socket. The disclosed kit and process also allows for the formation of a prosthetic socket directly on a residuum without the use of water to activate a hardenable material.

SUMMARY

In order to provide an improved process and kit for constructing a prosthetic socket, different embodiments are provided which pertain to an inventive process and kit for constructing a prosthetics socket. The kit includes an inner protective sheath, an outer protective sheath, and a web. The web may have at least one layer of elasticized fabric and multiple layers of braided fibers.

The kit may also include a prosthesis coupler element integrated with the web at a distal end of the web.

The kit may further be provided with an injection fitting for connecting to the prosthesis coupling element.

The kit can also include an injection material for forming the prosthetic socket, as well as an injection mechanism or device that injects the material through the injection fitting.

The kit may have a prosthetic liner and a protective film for wrapping the prosthetic liner.

According to one method, the kit is used in the following manner. An inner protective sheath is placed on a residual limb. A web is then placed over the inner protective sheath. An outer protective sheath is next placed over the web. Seals are then created between the inner and outer protective sheaths at both ends of the sheaths, thereby creating an enclosed zone or chamber around the web between the inner and outer protective sheaths. Material is injected into the chamber to form the prosthetic socket.

The process can also include the step of placing a prosthetic liner on the residual limb before the inner protective sheath is placed on the residual limb.

The process can also include providing a prosthesis coupler element on the web. The prosthesis coupler element may be tightened to the liner prior to placing the outer protective sheath on the residual limb.

The process can also include providing an injection fitting on the prosthesis coupler element prior to injecting the material into the enclosed zone.

The process can also include applying pressure around the outer protective sheath after injecting the material into the enclosed zone.

The prosthetic socket formed by this process includes a generally tubular web that has been impregnated with material and hardened, only after the web has been placed on the residual limb. Further, the prosthetic socket is impervious to the passage of liquids or gasses.

The material of the prosthetic socket can be a two-component, curable polyurethane resin, or other suitable resin. Alternatively, the material may be thermoformable or comprise Plaster-of-Paris.

The web may include multiple layers of braided fibers that may be glass, carbon fibers, or any other suitable fiber. The fibers may be oriented at suitable angles that can vary from layer to layer. The web can also include a prosthesis coupler element.

A number of advantages arise from the inventive kit, process and prosthetic socket, including the ability to form an airtight prosthetic socket directly on the residual limb. An important advantage of the kit and process is that the prosthetic socket can be formed without the use of water. This allows the prosthetic socket to be formed on the residual limb anywhere in the world, even where access to water is extremely limited, such as in many developing countries or in desert regions.

Of course, other methods, embodiments, and variations thereof are described in greater detail in the following discussion.

These and other features, aspects, and advantages of the present invention will become better understood with regard to the following description, appended claims, and accompanying drawings.

DETAILED DESCRIPTION OF VARIOUS EMBODIMENTS

A. Environment and Context of the Various Embodiments

Traditionally the formation of a prosthetic socket required numerous steps involving negative and positive molds, and casts that required manipulation and rectification by a highly trained prosthetist. The current kit and process substantially reduces the time and complexity involved in constructing a prosthetic socket.

In the past, the formation of most prosthetic sockets involved the use of Plaster-of-Paris, or some other water hardenable material, either to form the negative mold, or to construct the socket itself. The use of these materials require access to water, which is problematic in developing countries or desert regions where access to water may be limited.

Unfortunately, it is in a number of these regions where the need for prosthetic limbs is high, due to warring conflicts resulting in extensive landmine use and poor health care access. However, due to the cost and complexity involved in the creation of a typical prosthetic socket, including the typical requirement for access to water, many people with limb loss in developing countries go through life without replacement limbs.

The kit, process and prosthetic socket of the following disclosure provides elegant solutions to the above problems by providing a relatively simplistic kit and process that reduces the time and expertise required to create a prosthetic socket as well as eliminate the requirement for water.

For ease of understanding the kit, process and prosthetic socket disclosed herein, the following terms are described. As used herein, the term "proximal" has its ordinary meaning and refers to a location that is closer to the heart than another location. Likewise, the term "distal" has its ordinary meaning and refers to a location that is further from the heart than another location. Also, the terms "residual limb" and "residuum" are herein used interchangeably to refer to the remaining portion of a limb following the removal of part of the limb.

B. Detailed Description of an Embodiment

Figure 1:
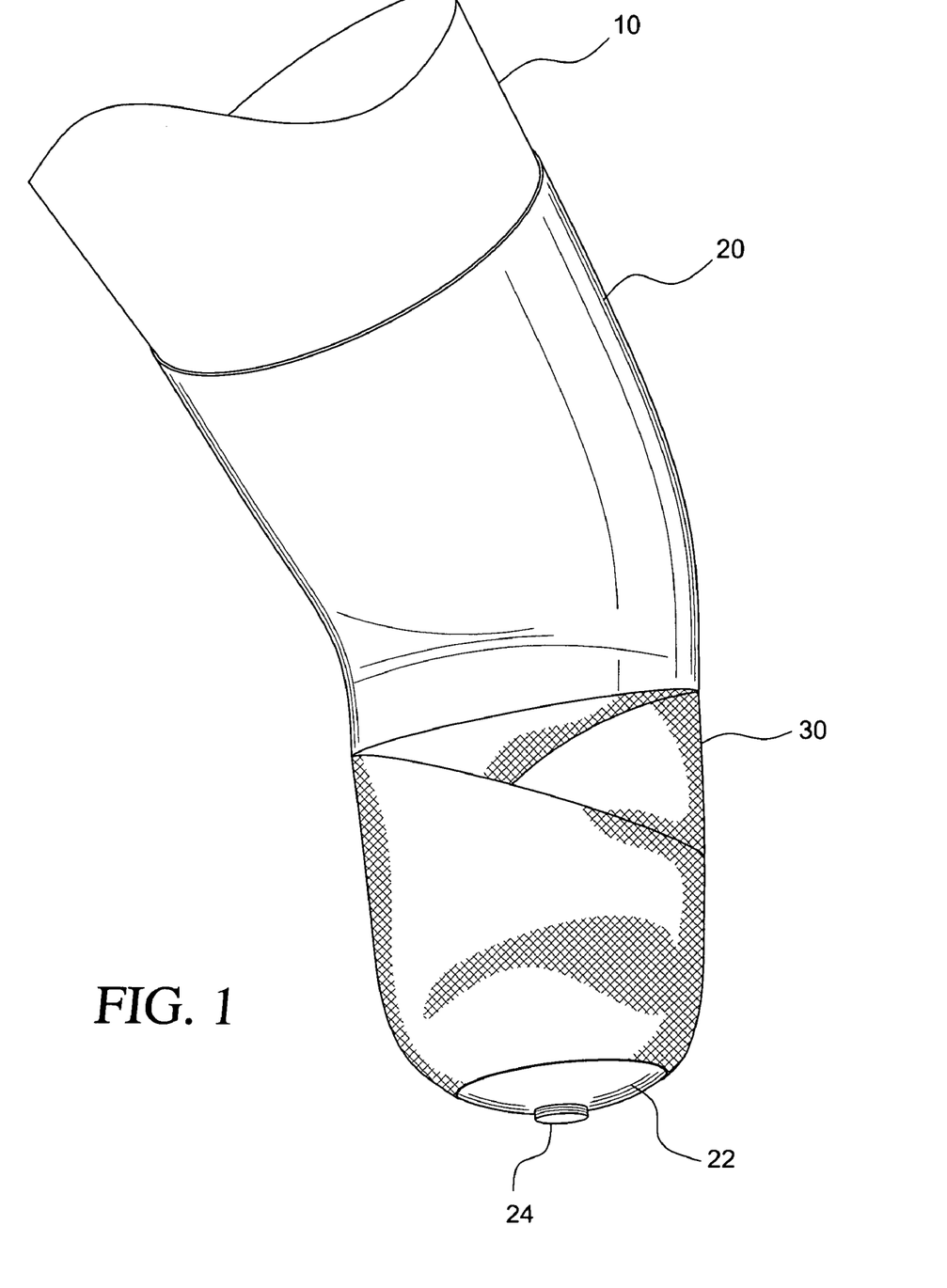
FIG. 1 is a side elevational view of a residual limb with initial preparations for constructing a prosthetic socket according to one embodiment.

A first step in implementing the process of forming the prosthetic socket is illustrated in FIG. 1. A prosthetic liner 20, typically a silicone liner of a type known in the art, is placed upon the residuum 10. The liner 20 may include a distal umbrella or cap 22 with a standard internally threaded boss part 24. Exemplary silicone liners are of the types disclosed in U.S. Pat. No. 6,136,039, granted Oct. 24, 2000 to Kristinsson et al., and U.S. Pat. No. 6,485,776, granted Nov. 26, 2002 to Janusson et al., both incorporated herein by reference.

The prosthetic liner 20 compresses the residuum into the appropriate shape required for complimenting the prosthetic socket in as comfortable a manner as possible. Further, a protective film or wrap 30 is wrapped around the distal end of the liner to additionally compress the residuum.

Figure 2:
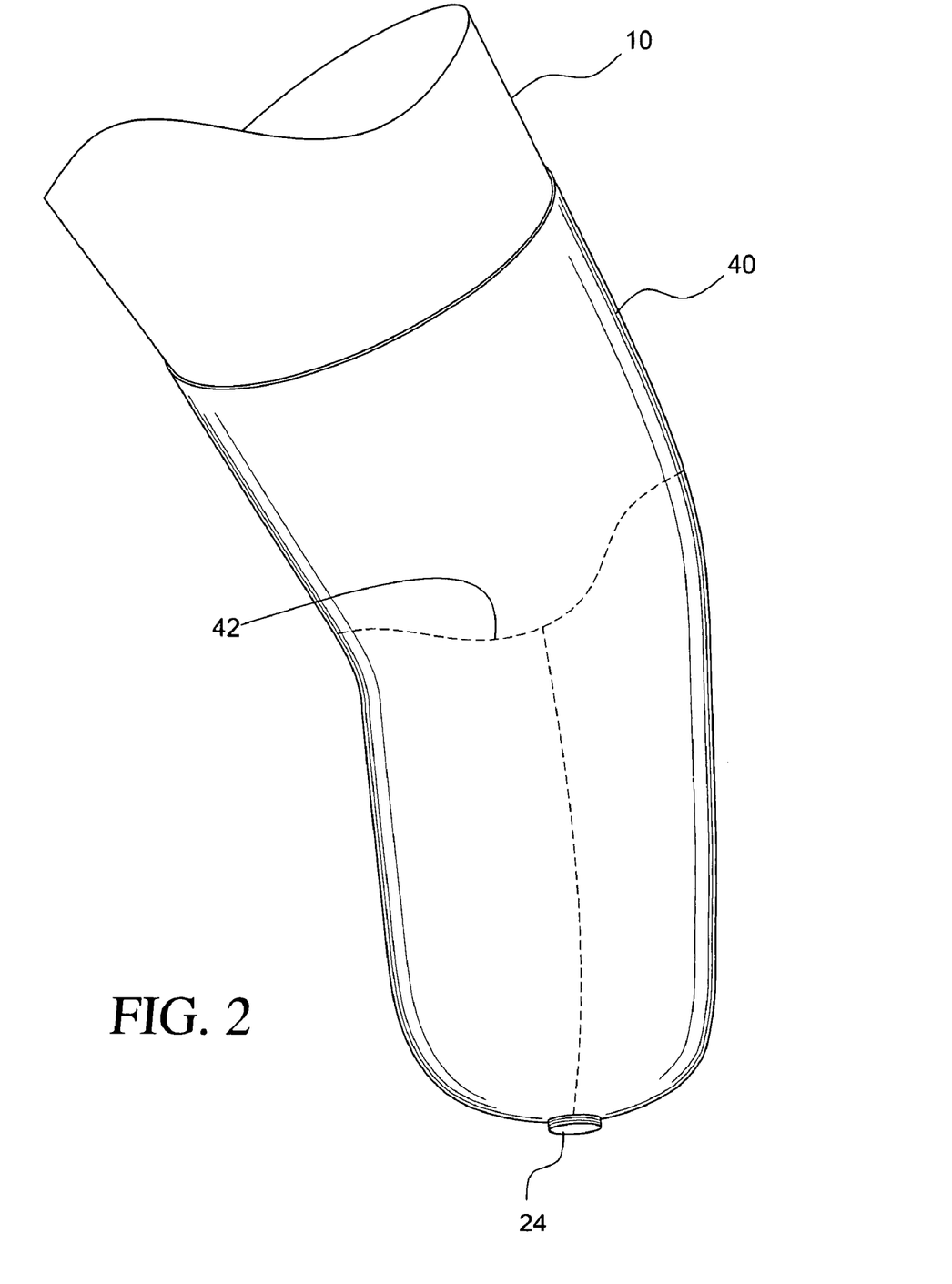
FIG. 2 is a side elevational view of a residual limb during an intermediate stage of constructing a prosthetic socket according to one embodiment.

A second step is illustrated in FIG. 2, where an inner protective sheath 40 is placed on the residuum. The inner protective sheath 40 may include an opening at the distal end that allows the internally threaded boss part 24 to protrude through the distal end thereof.

The inner protective sheath 40 may be in tubular form and constructed of any appropriate material that is impermeable to liquids and impervious to vapors. The inner protective sheath 40 may also have the ability to elastically deform around the liner 20 and the residuum 10. An exemplary material may be latex rubber, or any material having similar characteristics. The elastic stretching of the inner protective sheath 40 further compresses the residuum 10 into the appropriate complimentary shape for the prosthetic socket.

Trim lines 42 can be drawn or otherwise marked on the outer surface of the inner protective sheath 40 for later transfer onto the inner surface of the eventual prosthetic socket 100.

Figure 3:
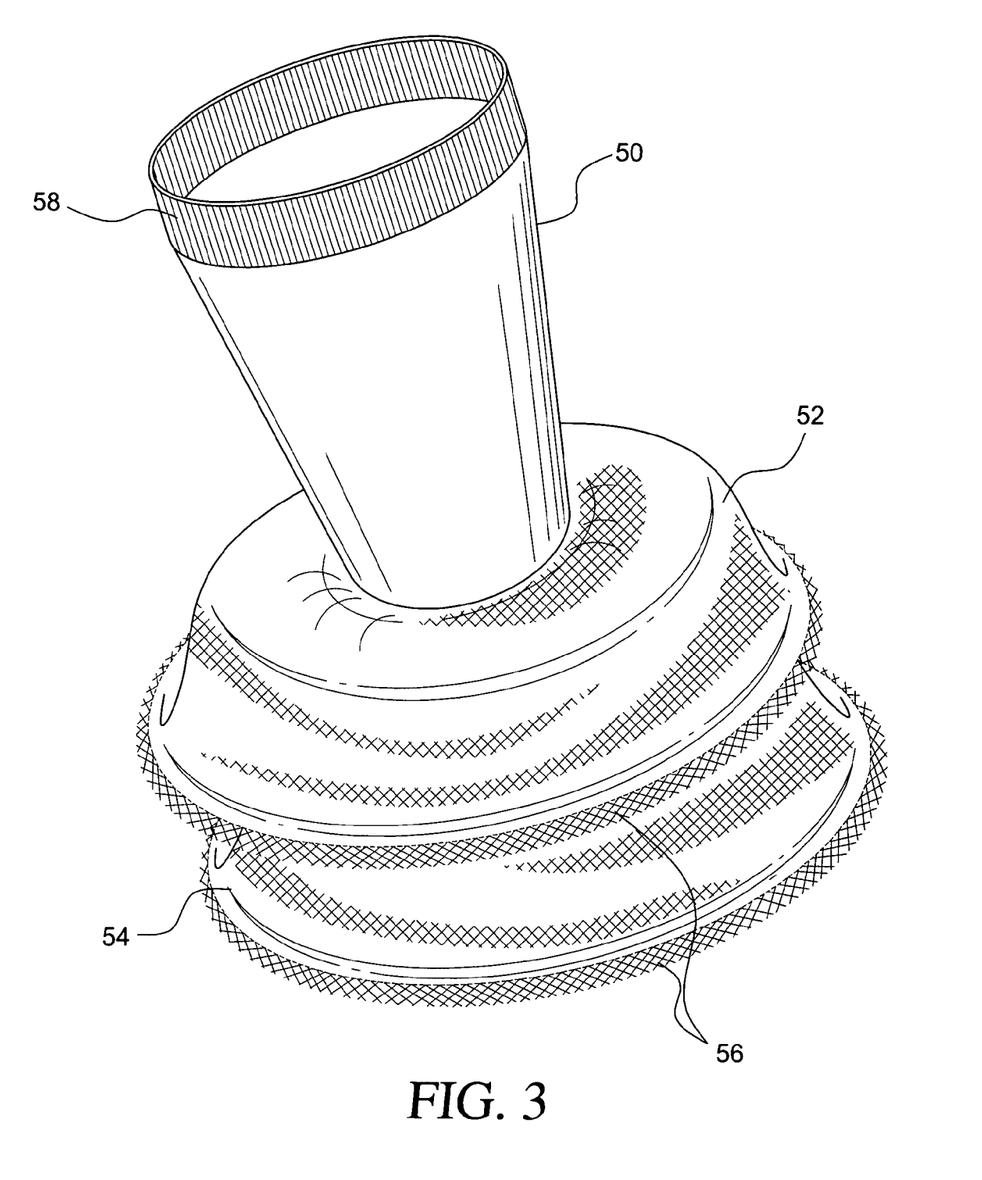
FIG. 3 is a side elevational view of a web for use in constructing a prosthetic socket according to one embodiment.

FIG. 3 illustrates an embodiment of a web 50 for use in the process of forming the prosthetic socket. The web 50 may be composed of an inner tubular layer of elasticized fabric, including an elastic band 58 at the proximal end of the web 50. The web 50 additionally has at least two layers 52, 54 of braided fibers which have loose ends 56 that can be trimmed.

The fibers in the at least two layers of braided fibers can be glass or carbon fibers, or any other suitable fiber. The fibers within each layer can be oriented with respect to each other at any suitable angle between 0 and 90 degrees. For example, the fibers within each layer could be oriented at an angle of 45 degrees relative to each other.

The fibers in each layer may be oriented at different angles from the fibers in each other layer. For example, in a two layer web, the fibers in one layer may be oriented at an angle of 45 degrees relative to the fibers in the other layer.

One advantageous feature of the web 50 is that the web is not pre-impregnated with a hardenable material requiring activation or hardening by water. Because the web 50 is not pre-impregnated, numerous disadvantages of pre-impregnated webs are avoided. For example, a typical pre-impregnated web must be wetted and stored in moist environment in a sealed package so that the web does not prematurely harden. These pre-impregnated webs must be moist in order to be manipulated into the appropriate shapes for the eventual hardened product. This leads to a complicated endeavor, since the moistened hardenable material that is pre-impregnated into the web may adhere to anything that it comes into contact.

Since the web 50 illustrated in FIG. 3 is not pre-impregnated with a hardenable material, the web 50 can easily be manipulated into position on the residuum and shaped into the appropriate form.

Figure 4:
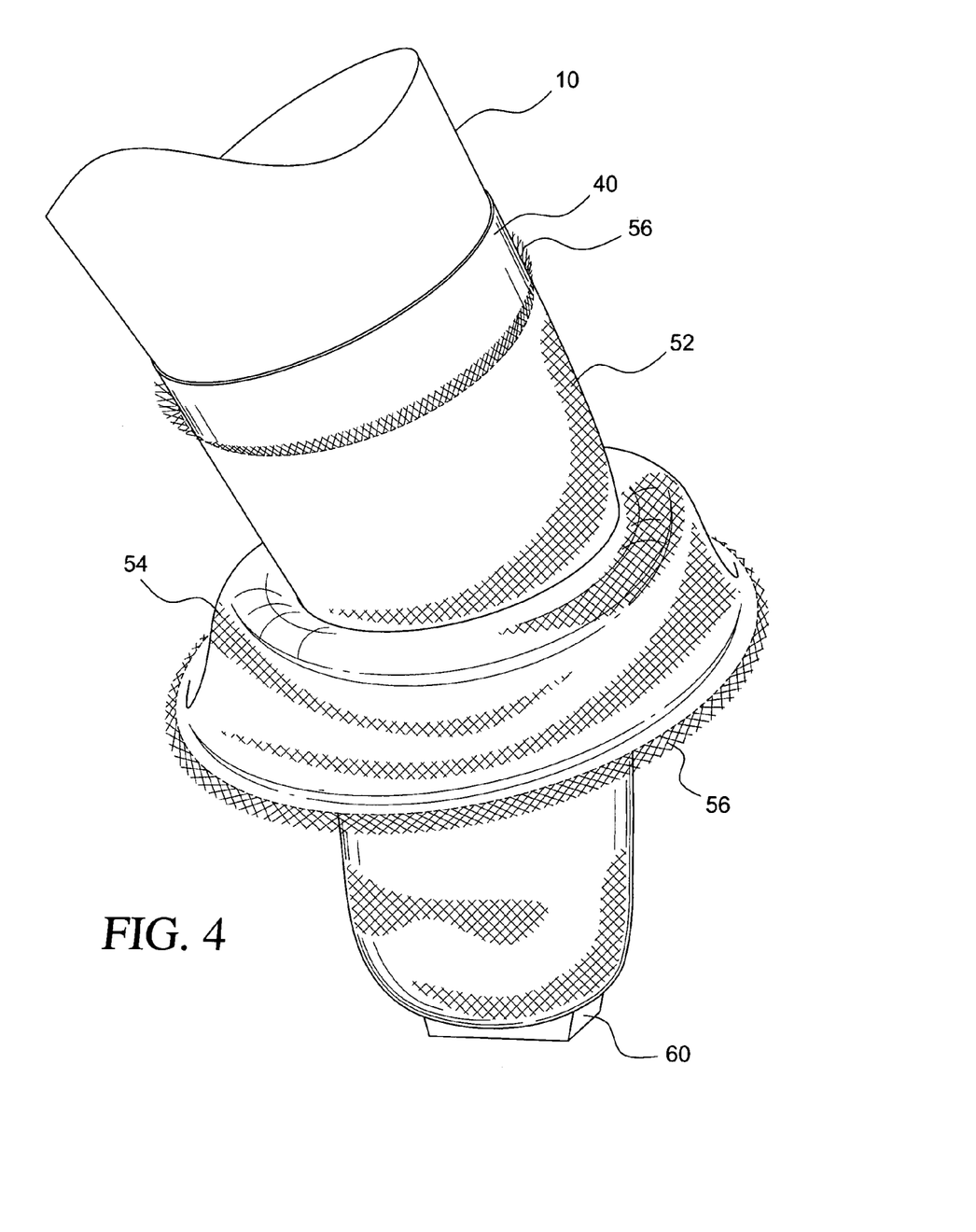
FIG. 4 is a side elevational view of a residual limb carrying the web of FIG. 3.

FIG. 4 illustrates the web 50 being placed into position on the residuum 10 over the inner protective sheath 40. Both layers of fibers 52, 54 can be clearly seen.

A prosthesis coupler element 60 may be connected or integrated into the distal end of the web 50 in any suitable manner, including adhesive or mechanical connections. The prosthesis coupler element 60 may be of any appropriate design, including known designs for coupling elements. However, the prosthesis coupler element 60 should be able to receive an injected material, as will be discussed below.

Figure 5:
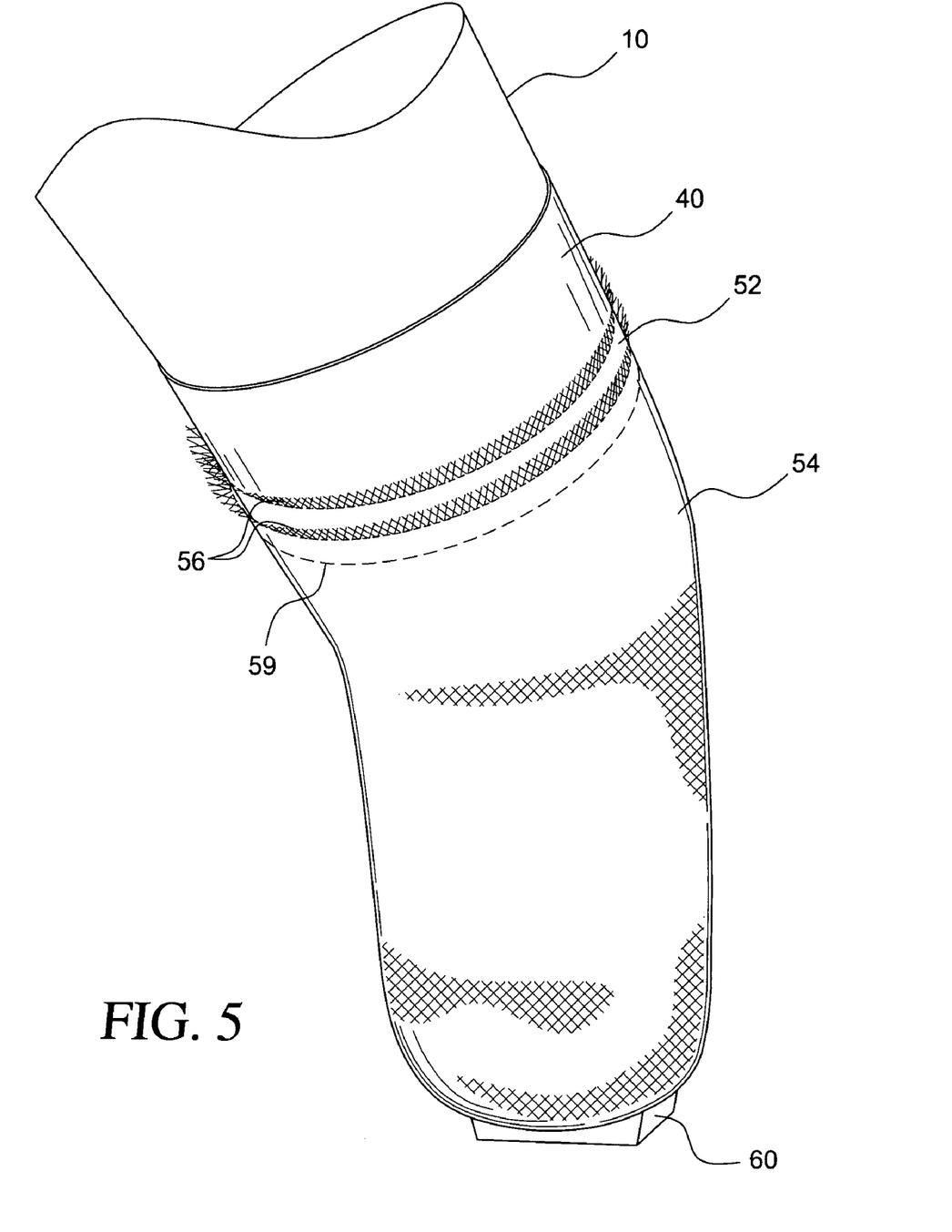
FIG. 5 is a side elevational view of a residual limb during an intermediate stage of constructing a prosthetic socket according to one embodiment.

In observing FIG. 5, after the web 50 is placed in position, the web may be marked 59 for the appropriate approximate length of the eventual prosthetic socket.

Figure 6:
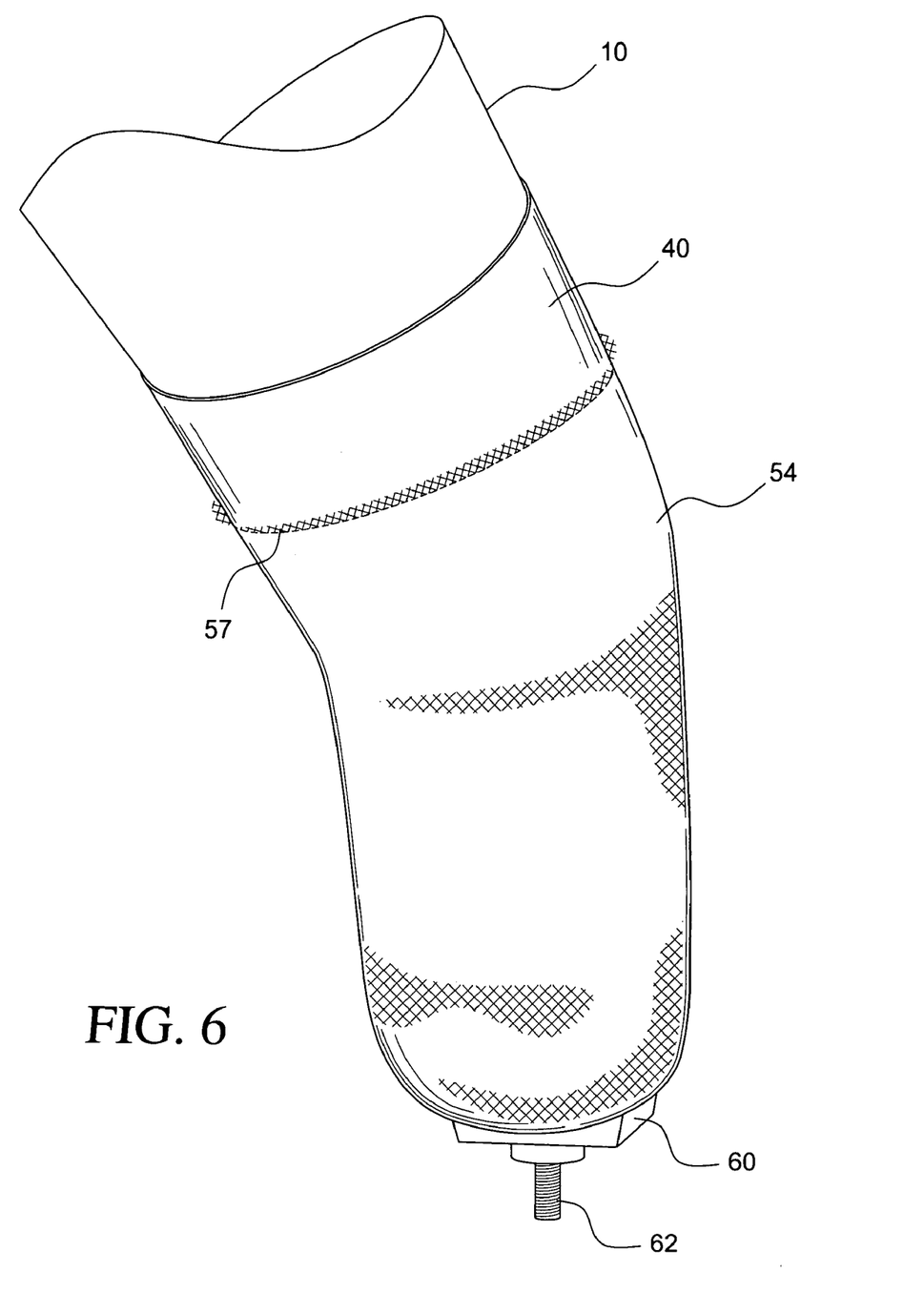
FIG. 6 is a side elevational view of a residual limb during an intermediate stage of constructing a prosthetic socket according to one embodiment.

Turning to FIG. 6 the web 50 may then be removed and the excess of the layers 52, 54 of the braided fibers may be trimmed, leaving the trimmed end 57. The web 50 is then placed back on the residuum 10 over the inner protective sheath 40. The prosthesis coupler element 60 is tightened against the residuum 10 by screwing a tightening screw 62 through the prosthesis coupler element 60 into the internally threaded boss member 24 on the liner 20.

Figure 7:
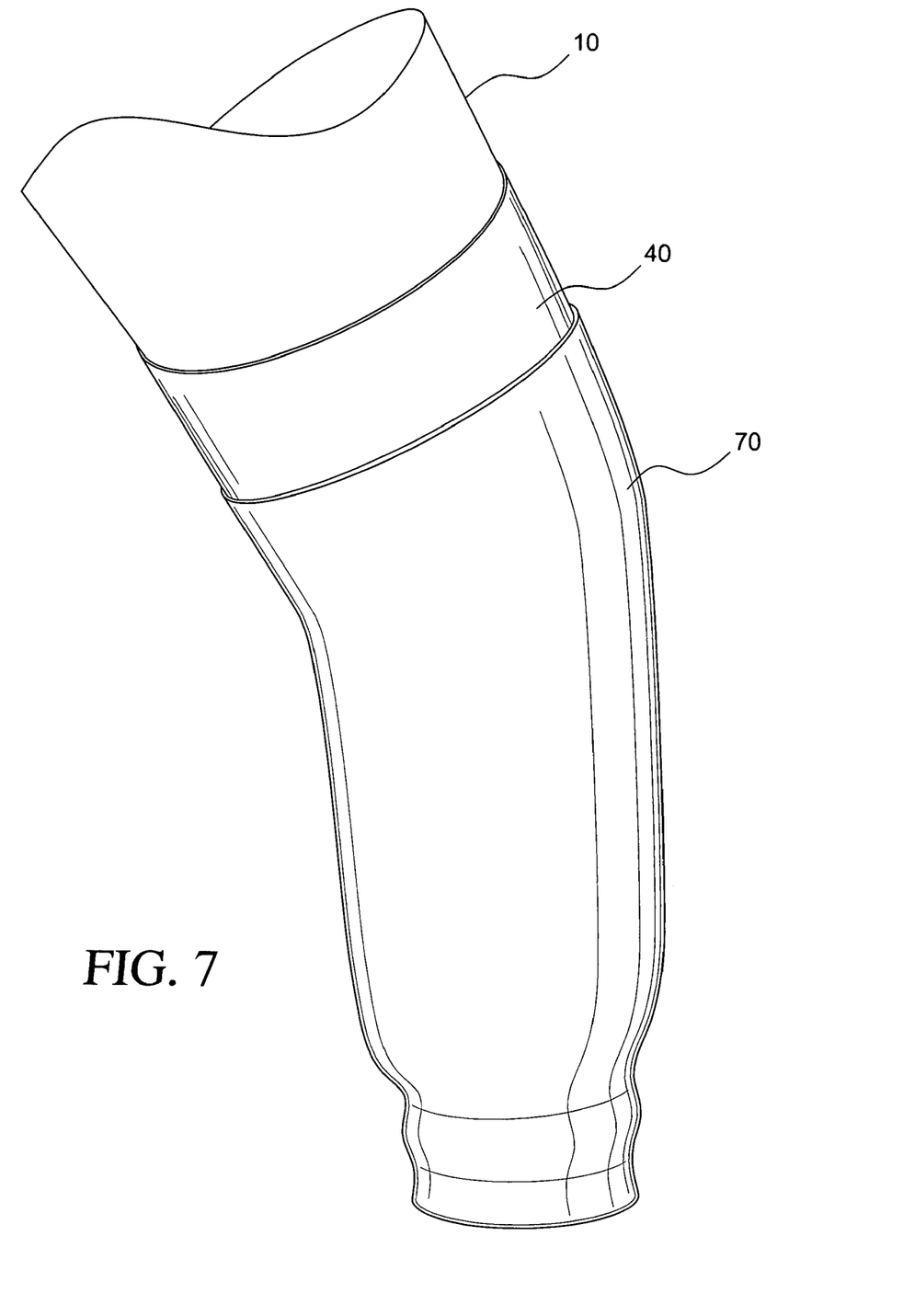
FIG. 7 is a side elevational view of a residual limb during an intermediate stage of constructing a prosthetic socket according to one embodiment.

Next, as shown in FIG. 7, an outer protective sheath 70 is placed over the web 50 and the residuum 10. The outer protective sheath can be constructed similarly to the inner protective sheath 40. The outer protective sheath 70 may be tubular, liquid and vapor impervious, and elastically deformable. Some suitable materials include latex rubbers and other materials having similar characteristics to latex rubbers. Other suitable sheaths include those having a construction with a polymeric material on one side, and a fabric on another side.

Figure 8:
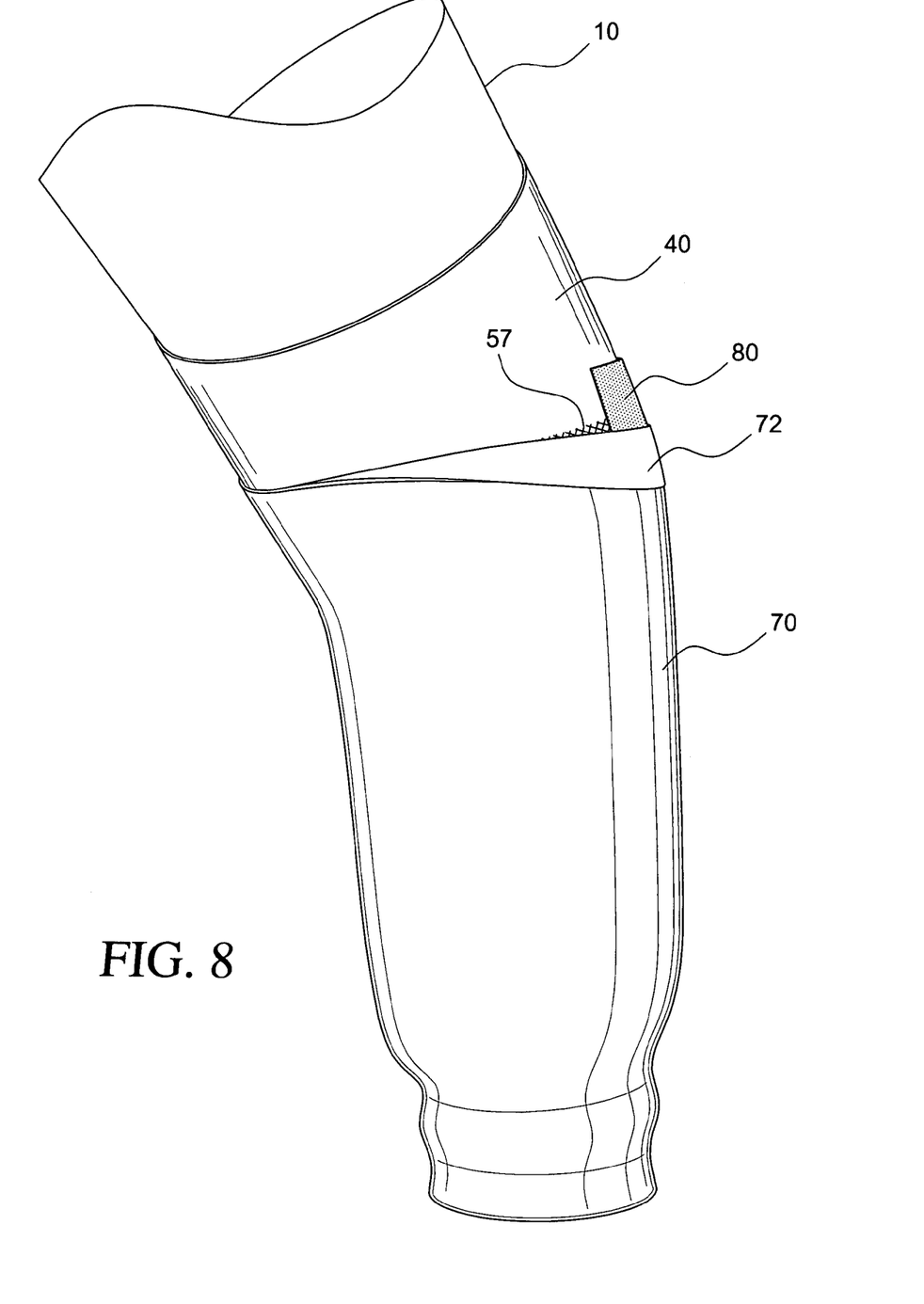
FIG. 8 is a side elevational view of a residual limb during an intermediate stage of constructing a prosthetic socket according to one embodiment.

In observing FIG. 8, the outer protective sheath 70 is folded over itself at the proximal end to form a first folded over flap 72. The folded over flap 72 exposes at least some of the trimmed ends 57 of the braided fibers. A breather 80 is placed between the inner protective sheath 40 and the outer protective sheath 70 in conjunction with the trimmed ends 57 of the braided fibers.

The breather 80 can be any suitable material, such as porous gauze, that allows the passage of excess material and gasses. The breather 80 may also comprise tubes or any other shape providing a communication channel for allowing the passage of excess material and gasses.

The breather 80 provides a communication path for excess material and gas to travel away from the trimmed ends 57 of the braided fibers. This allows the eventual socket to be formed in a uniform manner without trapping gas pockets within the hardened web.

Figure 9:
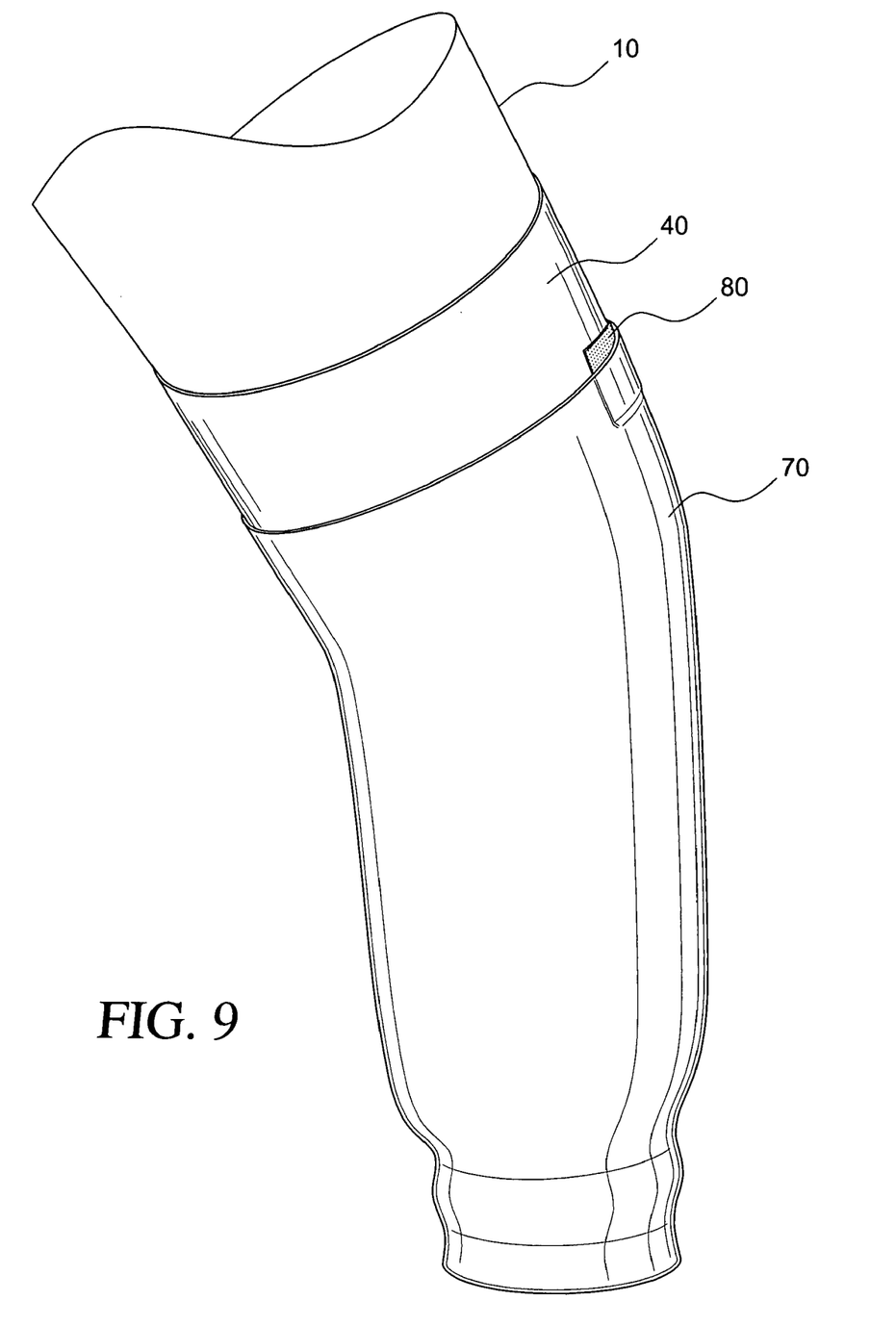
FIG. 9 is a side elevational view of a residual limb during an intermediate stage of constructing a prosthetic socket according to one embodiment.

As exemplified in FIG. 9, the first folded flap 72 of the outer protective sheath 70 is subsequently folded back to hold the breather between the inner protective sheath 40 and the outer protective sheath 70.

Figure 10:
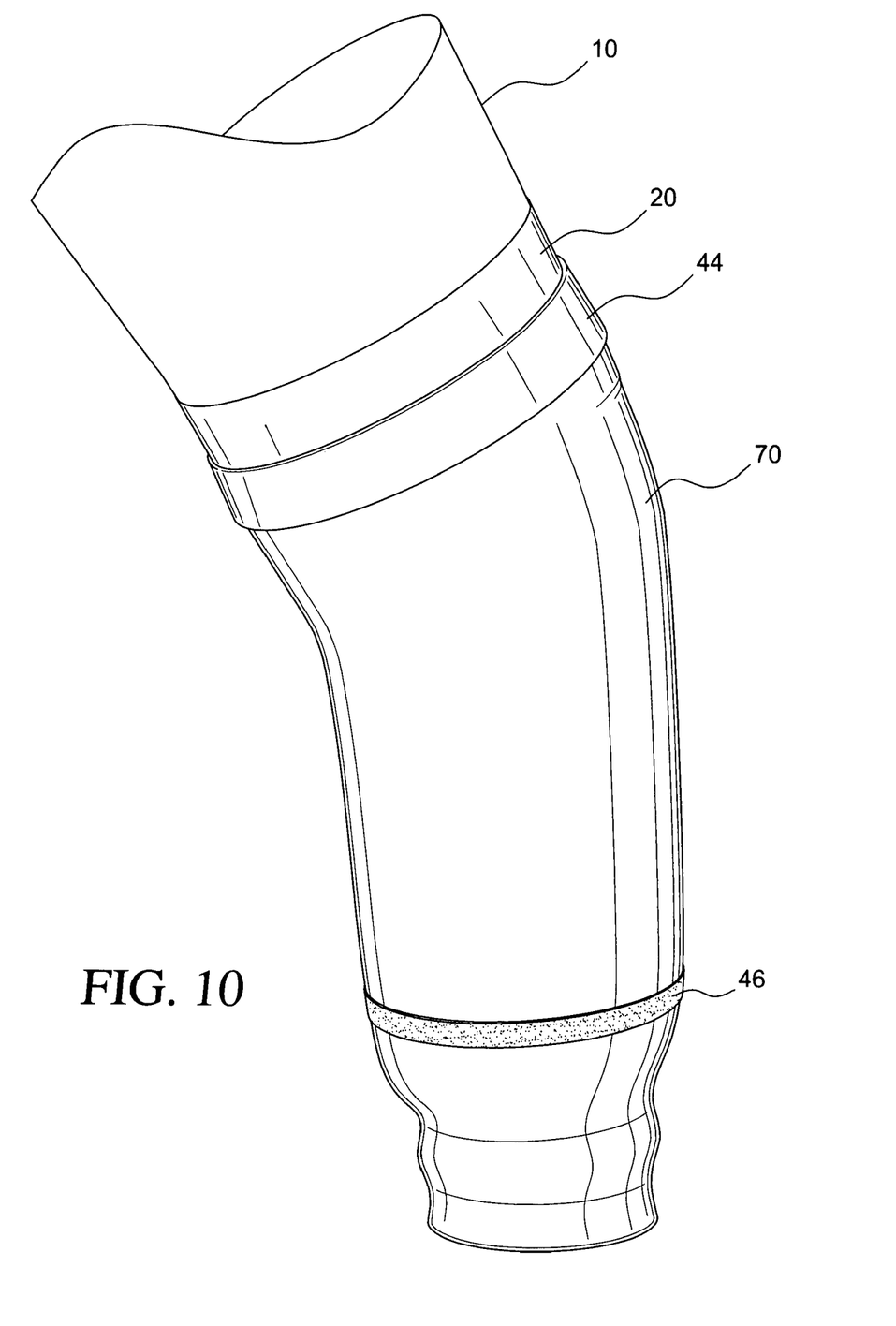
FIG. 10 is a side elevational view of a residual limb during an intermediate stage of constructing a prosthetic socket according to one embodiment.

Next, FIG. 10 illustrates how the proximal end of the inner protective sheath 40 is folded over both the breather 80 and the proximal end of the outer protective sheath 70 in order to create a proximal seal 44 between the inner protective sheath 40 and the outer protective sheath 70. An additional distal seal 46 may be created near the distal end of the outer protective sheath, for example, by providing a strip of adhesive tape, or any other suitable item, circumferentially around the outer protective sheath 70 near the distal end. The tape seals the outer protective sheath 70 against the web 50.

A chamber or enclosed zone is formed around the web 50 with the proximal and distal seals 44, 46. The chamber creates an enclosed space between the inner protective sheath 40 and the outer protective sheath 70, which encloses the web 50 and the breather 80. While the chamber is airtight, the chamber can increase in volume due to the elasticity of the inner and outer protective sheaths 40, 70.

As shown in FIG. 10, the excess distal portion of the outer protective sheath 70 is folded back over the distal seal 46 to create a second folded flap 74 of the outer sheath. Once the second flap 74 is folded back, the prosthesis coupler member 60 is made accessible. An injection fitting 64 is attached to the prosthesis coupler member 60 in any suitable fashion, such as by threading. An injection mechanism 90 is connected to the injection fitting 64 through a communication pathway 92, such as a tube or a hose.

The injection mechanism 90 may be any suitable device for injecting material into the chamber surrounding the web 50. An example of a suitable injection mechanism 90 includes a two component curable polyurethane injection gun known to those having ordinary skill in the art. An example of such an injection gun is shown in U.S. Pat. No. 6,484,904, granted Nov. 26, 2002 to Horner et al., incorporated herein by reference.

Figure 11:
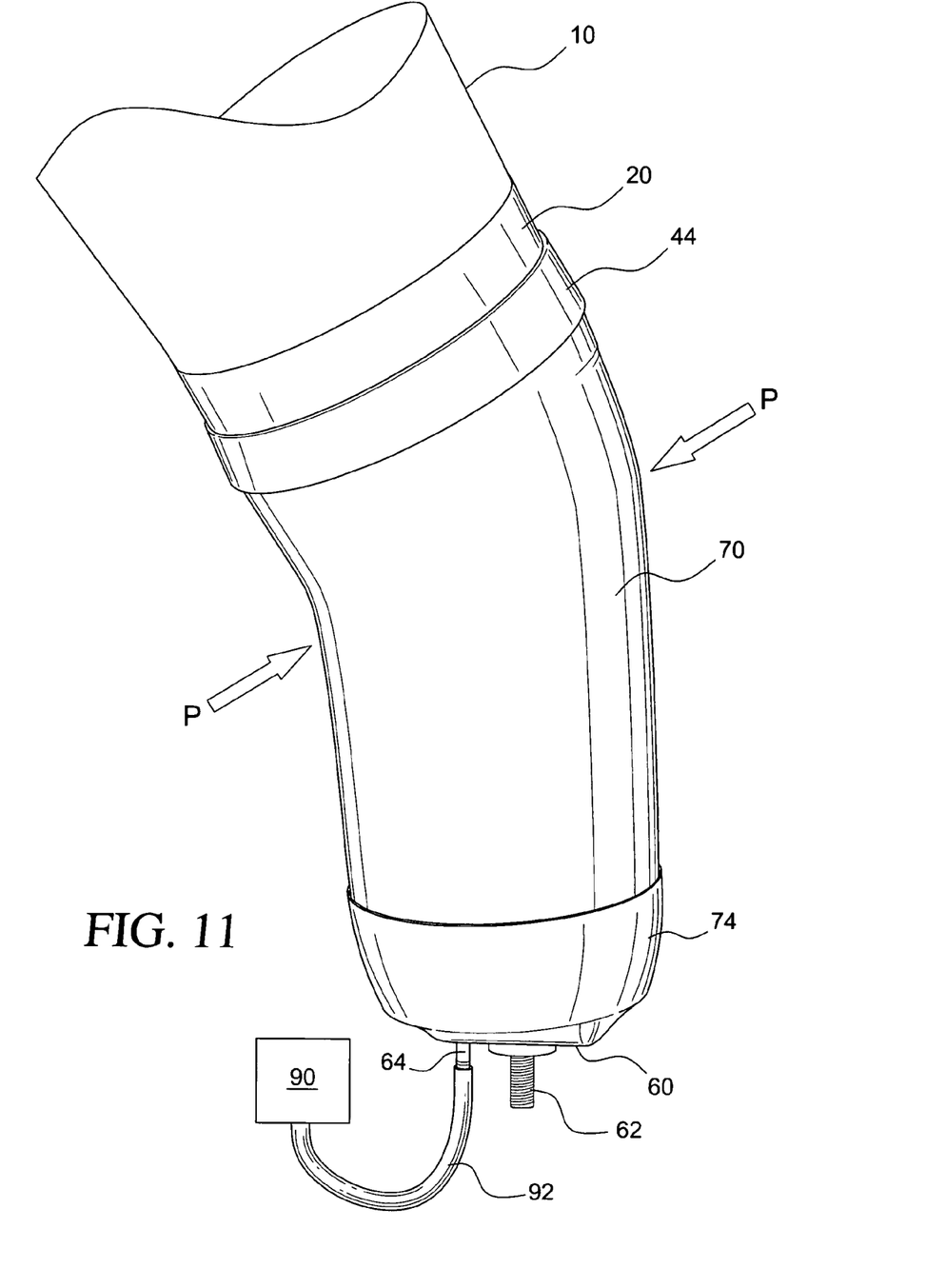
FIG. 11 is a side elevational view of a residual limb during the injection stage of constructing a prosthetic socket according to one embodiment.

One advantage of using a two component curable polyurethane injection system is that there is no need for access to water to activate and harden the web 50. The two components of the polyurethane are mixed in the nozzle of the injection gun and are injected simultaneously into the chamber around the web 50. Once enough material has been injected into the chamber, the outer protective sheath 70 is manually manipulated to ensure that that material is equally distributed through the chamber around the web 50, and also to ensure that the material impregnates the braided fibers 52, 54 of the web 50.

Figure 14:
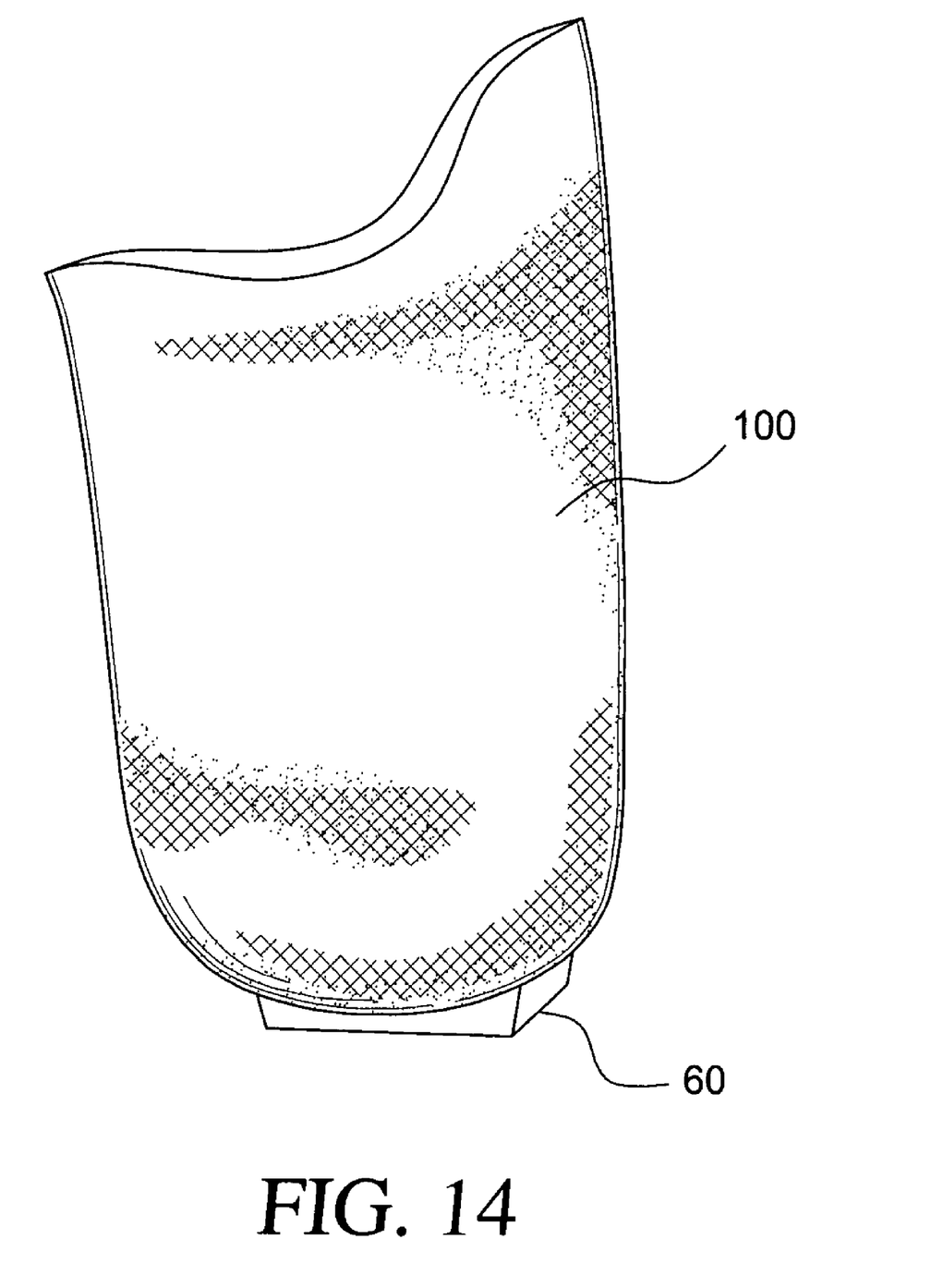
FIG. 14 is a side elevational view of a finished prosthetic socket constructed according to one embodiment.

Full impregnation of the injected material with the braided fibers 52, 54 of the web 50 provides for an integral prosthetic socket 100, as shown in FIG. 14. Because the injected material fully impregnates the braided fibers 52, 54 of the web 50, there are no pores or spaces between the braided fibers that could allow the passage of water or air. The eventual definitive prosthetic socket 100 is therefore water and air tight, and can be used with seal in liners of the type disclosed in U.S. Pat. No. 7,025,793, granted on Apr. 11, 2006 to Egilsson, and herein incorporated by reference.

Once the material has been generally equally distributed by manual manipulation, pressure P is externally applied to the outer protective sheath 70 while the two component polyurethane resin is curing. The pressure P can be applied in any number of ways, including the ICECAST™ technique discussed above and disclosed in U.S. Pat. No. 5,885,509. Pressure P can also be applied by wrapping a film or elastic bandage around the outer protective sheath 70, similarly to the wrapping of the silicone liner 20 as shown in FIG. 1.

Pressure P can also be applied by placing an additional silicone liner over the outer protective sheath 70. Continued manual manipulation may be used to apply the pressure P.

While this discussion has been in reference to a two component curable polyurethane, any appropriate material may be injected into the chamber around the web 50. Such materials include other curable resins, Plaster-of-Paris, glues or resins having a certain viscosity, or thermoformable materials. Further, any injection mechanism may be used, such as any type of pump or any plunger type dispenser.

In addition to the application of pressure P, when using a thermoformable material a temperature increase may be applied around the outer protective sheath 70 in order to harden and form the material. Since the web 50 and the outer protective sheath 70 are still located on the residuum, the temperatures used must be low enough to prevent burning of the underlying tissue of the residuum.

Alternatively, if the material is sufficiently hardened such that it will not lose its shape during removal from the residuum, higher temperatures may be used to fully harden and form the material.

Figure 12:
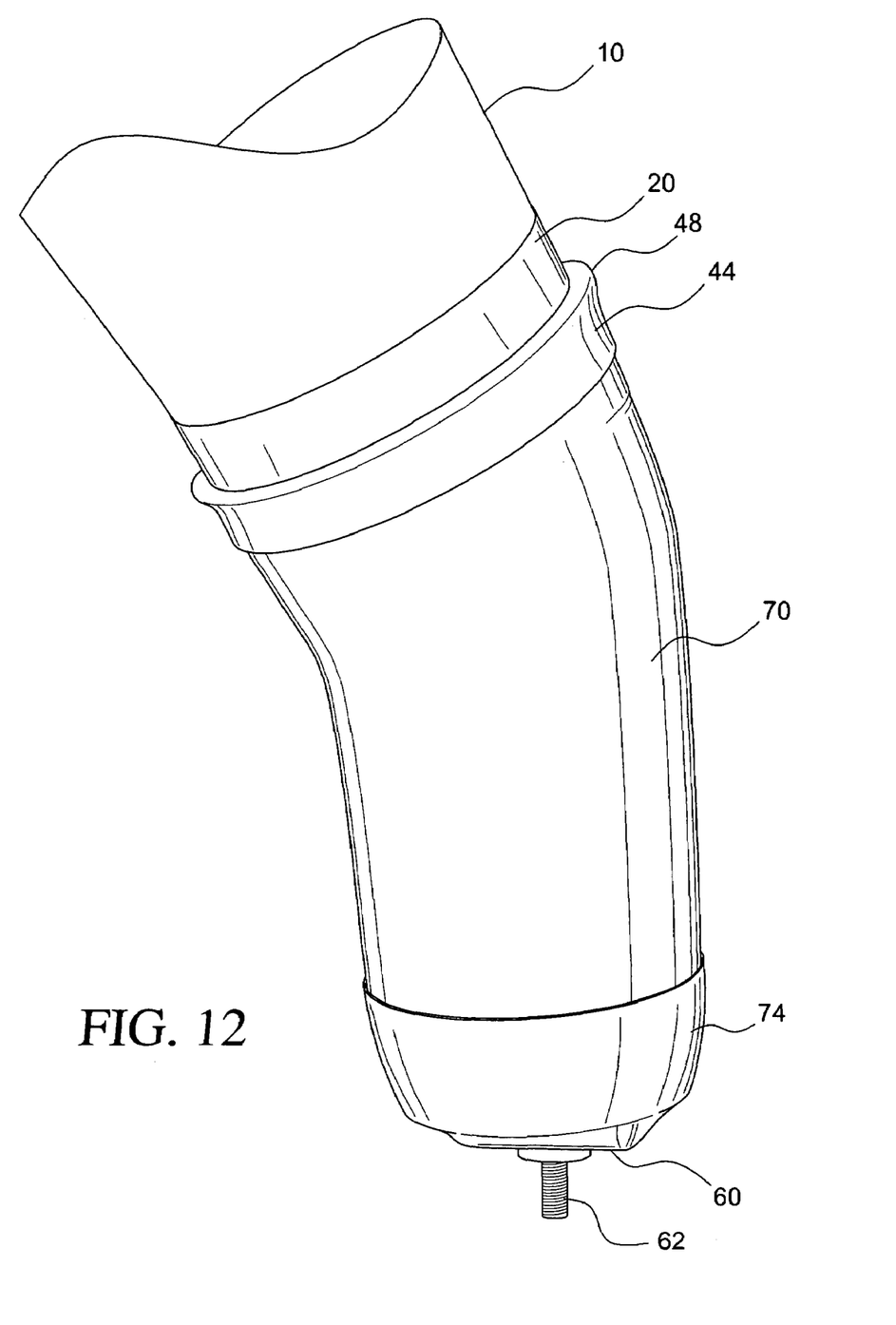
FIG. 12 is a side elevational view of a residual limb following the injection stage of constructing a prosthetic socket according to one embodiment.

As illustrated in FIG. 12, once the pressure P is removed and the material has cured or hardened sufficiently, excess material that has passed from the web 50 through the breather 80 collects and forms a bulge 48 in the region of the proximal seal 44.

Figure 13:
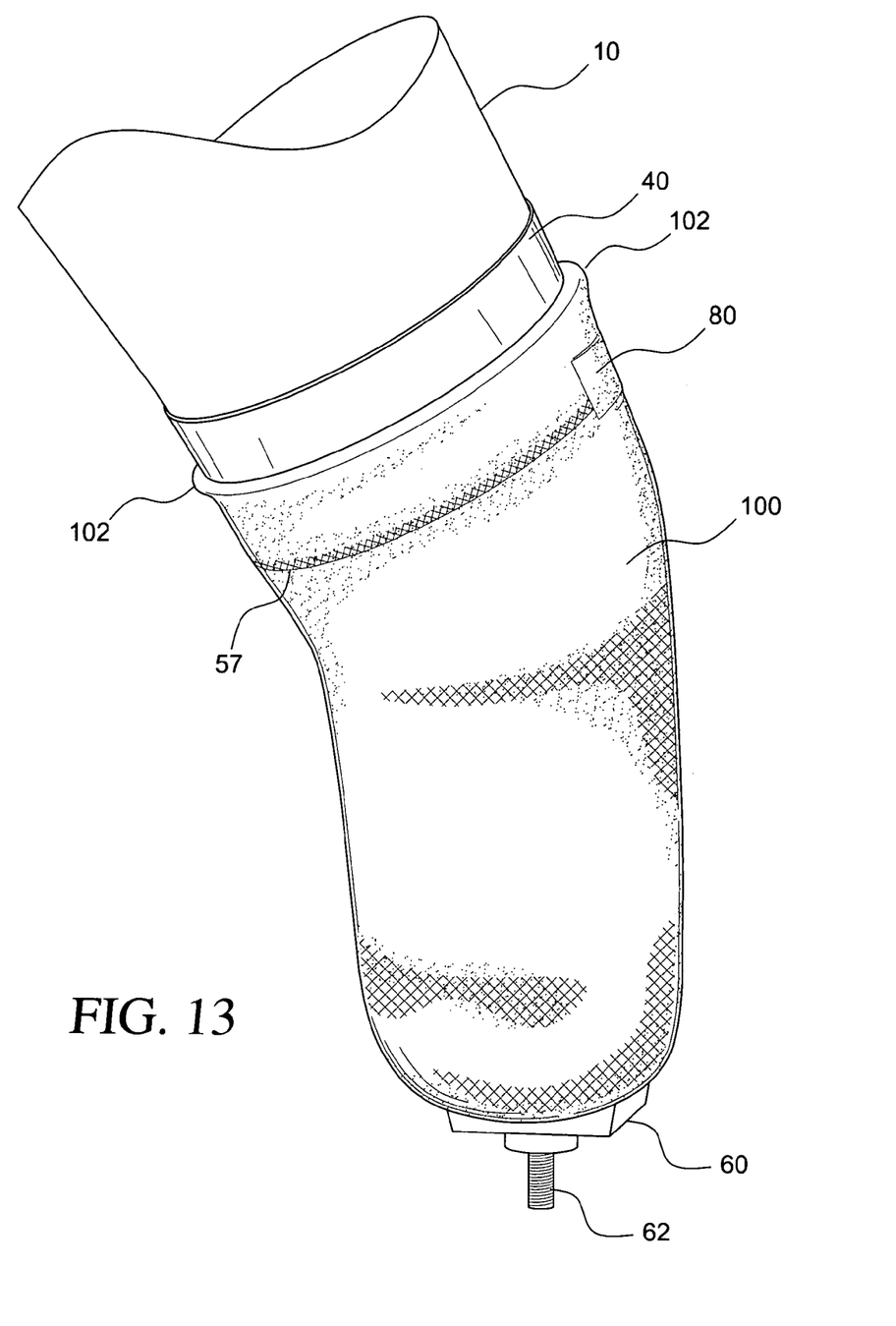
FIG. 13 is a side elevational view of a residual limb carrying an unfinished prosthetic socket constructed according to one embodiment.

Turning to FIG. 13, when the flap of the inner protective sheath 40 is folded back to remove the proximal seal 44, and the outer protective sheath 70 is removed, the excess material 102 can be seen. The excess material extends from about the trimmed ends 57 of the braided fibers and integrally through the breather 80. The use of the breather 80 allows the socket 100 to be formed uniformly, since the excess material is collected through the breather 80 and into the bulge 48.

In FIG. 14, the prosthetic socket 100 is shown removed in a completed state. At this point, the trim lines 42 have been transferred from the inner protective sheath 40 to the inner surface of the prosthetic socket 100. The definitive prosthetic socket 100 is trimmed along the transferred trim lines to produce the final form of the prosthetic socket 100.

As previously discussed, the injected material impregnates and integrates with the web 50 to create a water and airtight prosthetic socket 100 that can be used directly with seal in liners. The completed socket 100 can be formed without the use of water, thereby allowing people in developing countries and regions with limited access to water, easier access to the use of replacement limbs.

The necessary components required to carry out the process of forming the definitive prosthetic socket 100 may be provided in a kit. For example, the kit may comprise the inner protective sheath 40, the outer protective sheath 70, and the web 50. The kit may also include the prosthesis coupler element 60, the injection fitting 64, injection material, and the injection mechanism 90. The kit can include every component discussed above, including a prosthetic liner 20, protective film or wrapping 30, breather 80, and adhesive tape for creating distal seal 46.

C. Alternate Embodiments

The kit, process and prosthetic socket described herein are not limited to the specific structures, components, and steps described, but are merely illustrative in nature. As previously mentioned, numerous materials may be used in the construction of the prosthetic socket, including, but not limited to, carbon fiber, glass fiber, resins, epoxies, Plaster-of-Paris, and thermoformable materials.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various features from different embodiments and method steps. In addition to the variations described herein, other known equivalents for each feature can be mixed and matched by one of ordinary skill in this art to provide a kit for and perform a method of forming a prosthetic socket in accordance with the principles of the present invention.

Although this invention has been disclosed in the context of certain preferred embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims below.

The invention claimed is:

1. A method for forming a prosthetic socket directly on a residuum, the method comprising the steps of:
    placing an inner protective sheath over a residuum;
    placing a web over the inner protective sheath;
    placing an outer protective sheath over the web;
    forming a first seal at a proximal end between the inner and outer protective sheaths;
    forming a second seal at a distal end between the inner and outer protective sheaths;
    wherein an enclosed zone is formed around the web between the inner and outer protective sheaths; and
    injecting material into the enclosed zone to form the prosthetic socket.

2. The method of forming a prosthetic socket according to claim 1, further comprising the step of:
placing a liner on the residuum prior to placing the inner protective sheath over a residuum.

3. The method of forming a prosthetic socket according to claim 2, further comprising the step of:
placing a prosthesis coupler element on the web prior to placing the web over the inner protective sheath.

4. The method of forming a prosthetic socket according to claim 3, further comprising the step of:
tightening the prosthesis coupler element to the liner prior to placing the outer protective sheath over the web.

5. The method of forming a prosthetic socket according to claim 4, further comprising the step of:
placing an injection fitting on the prosthesis coupler element prior to injecting material into the enclosed zone.

6. The method of forming a prosthetic socket according to claim 1, further comprising the step of:
applying pressure around the outer protective sheath, after injecting material into the enclosed zone.

7. The method of forming a prosthetic socket according to claim 1, further comprising the step of:
placing a breather between the inner and outer protective sheaths, prior to creating the first seal.

8. The method of forming a prosthetic socket according to claim 1, further comprising the step of:
removing the outer protective sheath from around the formed prosthetic socket;
removing the prosthetic socket from around the inner protective sheath; and
trimming excess material from the prosthetic socket.

9. A kit for forming a prosthetic socket directly on a residuum, the kit comprising:
an inner protective sheath;
an outer protective sheath;
a web having a plurality of fibers capable of receiving a hardenable material;
and a hardenable material for impregnating the plurality of fibers of the web.

10. The kit for forming a prosthetic socket of claim 9, further comprising:
a prosthesis coupler element;
a breather having an air permeable structure; and
an injection fitting for permitting passage of the hardenable material therethrough.

11. The kit for forming a prosthetic socket of claim 9, further comprising:
a silicone liner that is air and moisture impervious; and
protective wrapping film arranged for wrapping about the liner.

12. A kit for forming a prosthetic socket directly on a residuum, the kit comprising:
a generally tubular web;
an inner protective sheath;
an outer protective sheath; and
a hardenable material for impregnating the web.

13. A kit for forming a prosthetic socket according to claim 12, wherein the hardenable material is a two component, curable polyurethane resin.

14. A kit for forming a prosthetic socket according to claim 12, wherein the hardenable material is Plaster-of-Paris.

15. A kit for forming a prosthetic socket according to claim 12, wherein the web comprises:
at least one layer of braided fibers.

16. A kit for forming a prosthetic socket according to claim 15, wherein the braided fibers are glass fibers or carbon fibers.

17. A kit for forming a prosthetic socket according to claim 15, wherein the braided fibers are oriented relative to each other at an angle of between 0 degrees and 90 degrees.

18. A kit for forming a prosthetic socket according to claim 15, wherein the web further comprises:
a prosthesis coupler element attached to a distal end of the web.

19. A kit for forming a prosthetic socket according to claim 12, wherein the web comprises a first layer of braided fibers oriented in a first direction and a second layer of braided fibers oriented in a second, different direction.

20. A kit for forming a prosthetic socket according to claim 12, further comprising:
an injection system for impregnating the hardenable material into the web.

* * * * *